(12) United States Patent
Young et al.

(10) Patent No.: US 11,143,655 B1
(45) Date of Patent: Oct. 12, 2021

(54) SYSTEMS AND METHODS FOR ASSAY PROCESSING

(71) Applicant: Theranos, Inc., Palo Alto, CA (US)

(72) Inventors: Daniel Young, Palo Alto, CA (US); Chinmay Pangarkar, Palo Alto, CA (US)

(73) Assignee: Labrador Diagnostics LLC, Wilmington, DE (US)

( * ) Notice: Subject to any disclaimer, the term of this patent is extended or adjusted under 35 U.S.C. 154(b) by 776 days.

(21) Appl. No.: 15/200,776

(22) Filed: Jul. 1, 2016

Related U.S. Application Data (60) Provisional application No. 62/187,809, filed on Jul. 1, 2015, provisional application No. 62/187,811, filed on Jul. 1, 2015.

(51) Int. Cl.
  *G01N 33/569* (2006.01)
  *G01N 1/28* (2006.01)

(52) U.S. Cl.
  CPC ....... *G01N 33/56983* (2013.01); *G01N 1/286* (2013.01); *G01N 2469/20* (2013.01)

(58) Field of Classification Search
  CPC .......... G01N 33/574; G01N 33/56983; G01N 1/286; G01N 2469/20
  See application file for complete search history.

(56) References Cited

U.S. PATENT DOCUMENTS

| | | | | |
|---|---|---|---|---|
| 2006/0292557 | A1* | 12/2006 | Su | C07K 14/005 435/5 |
| 2009/0286286 | A1* | 11/2009 | Lim | B82Y 30/00 435/91.2 |
| 2010/0218622 | A1* | 9/2010 | Motadel | B01L 3/0279 73/864.01 |
| 2014/0073043 | A1* | 3/2014 | Holmes | G01N 35/00 435/287.3 |

OTHER PUBLICATIONS

Singh et al. Laboratory Diagnosis of Herpes Simplex Virus. Canadian STI Best Practices Guidlines.2014.92-98.*

* cited by examiner

*Primary Examiner* — Rebecca M Fritchman

(57) ABSTRACT

Methods for obtaining a sample from a subject include providing a sample collection room within a retail store; and obtaining a sample from a subject at a retail location. Sample collection rooms may house a sample analysis device or system. Samples may be small, e.g., a finger-stick capillary blood sample.

5 Claims, 1 Drawing Sheet

Regression Analysis for Matrix Equivalency Study

Regression Analysis for Matrix Equivalency Study

SYSTEMS AND METHODS FOR ASSAY PROCESSING

CROSS-REFERENCE TO RELATED APPLICATIONS

This application claims priority to U.S. Provisional Application Ser. No. 62/187,809 filed Jul. 1, 2015 and U.S. Provisional Application Ser. No. 62/187,811 filed Jul. 1, 2015, both fully incorporated herein by reference for all purposes.

BACKGROUND

Clinical samples are useful in many situations, including being useful for monitoring the health of subjects, for diagnosing diseases or pathological conditions, and for monitoring the progress of therapeutic interventions, among various uses.

Obtaining clinical samples is desirable for such uses; however, subjects may find challenges with traditional laboratory testing.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY

Improved methods for obtaining clinical samples include providing a designated location in a point-of-service site where a clinical sample may be provided for analysis. In embodiments, improved methods for obtaining clinical samples include providing a designated location in a retail store, where the designated location is configured for obtaining a clinical sample; and obtaining a clinical sample from a subject. In embodiments, the sample may be analyzed at the same location; or at an adjacent location; or may be sent to a different location for analysis. In embodiments, the sample may be analyzed by an automatic analysis device or system at the same location; or at an adjacent location; or at a different location. A designated location in a retail store may be a sample collection room.

Applicants disclose methods for obtaining a sample from a subject, comprising providing a sample collection room in a retail store; and collecting a sample from a subject. Applicants disclose methods for obtaining a sample from a subject, comprising providing a sample collection room in a retail store; warming a fingertip, or finger, or hand of the subject; collecting a sample from a subject; and obtaining the sample. Applicants disclose methods for obtaining a sample from a subject, comprising providing a sample collection room in a retail store, the sample collection room comprising a warming table; warming a fingertip, or finger, or hand of the subject; and obtaining a sample from the subject. Applicants disclose methods for obtaining a sample from a subject, comprising providing a sample collection room in a retail store, the sample collection room comprising a chair; warming a fingertip, or finger, or hand of the subject; and obtaining a sample from the subject. Applicants disclose methods for obtaining a sample from a subject, comprising providing a sample collection room in a retail store, the sample collection room comprising a chair having a warming plate or other warming element; warming a fingertip, or finger, or hand of the subject; and obtaining a sample from the subject. Applicants disclose methods for obtaining a sample from a subject, comprising providing a sample collection room in a retail store, the sample collection room comprising an air-warmer; warming a fingertip, or finger, or hand of the subject; and obtaining a sample from the subject.

In embodiments, the sample is a small sample. For example, in embodiments of the methods for obtaining a sample from a subject, the sample is obtained from a finger-stick. For example, in embodiments, the sample comprises a few drops, or two drops, or one drop, of blood obtained from a small lancet puncture in the skin of the subject. For example, in embodiments, the sample is a small volume sample of blood, or of urine, or of saliva, or of tears, or other bodily secretion or excretion. For example, in embodiments, the sample is a small sample having a volume of less than about 200 µL, or less than about 150 µL, or less than about 100 µL, or less than about 75 µL, or less than about 50 µL, or less than about 25 µL, or less.

Applicants disclose methods for analyzing a sample obtained from a subject, comprising providing a sample collection room in a retail store; collecting a sample from a subject; and analyzing the sample. Applicants disclose methods for analyzing a sample obtained from a subject, comprising providing a sample collection room in a retail store; warming a fingertip, or finger, or hand of the subject; collecting a sample from a subject; and analyzing the sample. Applicants disclose methods for analyzing a sample obtained from a subject, comprising providing a sample collection room in a retail store, the sample collection room comprising a warming table; warming a fingertip, or finger, or hand of the subject; collecting a sample from a subject; and analyzing the sample. Applicants disclose methods for analyzing a sample obtained from a subject, comprising providing a sample collection room in a retail store, the sample collection room comprising a chair; warming a fingertip, or finger, or hand of the subject; collecting a sample from a subject; and analyzing the sample. Applicants disclose methods for analyzing a sample obtained, from a subject, comprising providing a sample collection room in a retail store, the sample collection room comprising a chair having a warming plate or other warming element; warming a fingertip, or finger, or hand of the subject; collecting a sample from a subject; and analyzing the sample. Applicants disclose methods for analyzing a sample obtained from a subject, comprising providing a sample collection room in a retail store, the sample collection room comprising an air-warmer; warming a fingertip, or finger, or hand of the subject; collecting a sample from a subject; and analyzing the sample. Applicants disclose methods for analyzing a sample obtained from a subject, comprising any of the foregoing methods, and providing the subject with a fingertoy, or placing a fingertoy on a finger of a subject following obtaining a sample from the subject. It will be understood that a step of warming a fingertip, or finger, or hand of a subject may comprise warming by use of a warming table, or warming plate, or air-warmer, or other warming device, or a combination thereof. It will be understood that the foregoing methods may be used together, and may be used in any combination.

In embodiments, the sample is analyzed at, or adjacent to, or near to, the sample collection room in the retail store. In embodiments, the sample is analyzed at a location other than at the retail store. In embodiments of the methods for analyzing a sample obtained from a subject, the sample is a small sample. For example, in embodiments, the sample is obtained from a finger-stick. For example, in embodiments, the sample comprises a few drops, or two drops, or one drop, of blood obtained from a small lancet puncture in the skin of the subject. For example, in embodiments, the sample is a small volume sample of blood, or of urine, or of saliva, or of tears, or other bodily secretion or excretion. For example, in embodiments, the sample is a small sample having a volume of less than about 200 µL, or less than about 150 µL, or less than about 100 µL, or less than about 75 µL, or less than about 50 µL, or less than about 25 µL or less.

Accordingly, Applicants disclose methods for obtaining and analyzing a sample obtained from a subject, comprising: providing a sample collection room in a retail store; collecting a sample from a subject in the sample collection room; and analyzing the sample. Applicants disclose methods for obtaining and analyzing a sample obtained from a subject, comprising: providing a sample collection room in a retail store; collecting a small sample from a subject in the sample collection room; and analyzing the small sample. Applicants disclose methods for obtaining and analyzing a sample obtained from a subject, comprising: providing a sample collection room in a retail store; collecting a sample from a subject in the sample collection room; and analyzing the sample at the retail store location, or adjacent to the retail store location.

In embodiments, a sample collection room may include a comfortable chair or seating location for a subject, e.g., for use by a subject during collection of a sample from the subject. In embodiments, a comfortable chair may be a reclining chair, having an upright configuration and a reclined configuration. In embodiments, a comfortable chair may be a reclining chair having an upright configuration and a plurality of reclined configurations. In embodiments, a sample collection room may include a refrigerator, a cabinet, a sink, storage units, a work surface configured for writing, and other furniture and architectural elements.

In embodiments, a sample collection room may include a sample analysis device or system; such a sample analysis device or system may be an automated sample analysis device or system, or may be a semi-automated sample analysis device or system. In embodiments, a sample collection room may include a computer, computer accessories, communication equipment and capability effective to link a computer, cell phone, or other device with WiFi, internet, cable, or other connections.

Accordingly, Applicants disclose herein systems comprising a room in a retail location, the room being configured for obtaining a clinical sample such as a blood sample. In embodiments, such systems comprise a room in a retail location, the room being configured for obtaining a clinical sample such as a blood sample, the room including one or more of a warming table, a calming feature, a chair, a pass-through to an adjacent bathroom, adjustable lighting, calming scents, and a sound source providing calming sounds. In embodiments, the chair is a reclining chair. In embodiments, the system includes an adjacent bathroom.

In embodiments, the sample collection room may be part of a sample collection center, or wellness center, including a waiting room and a sample collection room. In embodiments, a sample collection room, or wellness center, may include a waiting room, a sample collection room, and a bathroom. In embodiments, a bathroom that is part of a sample collection room, or wellness center, may include a sink (e.g., for handwashing) and a toilet. In embodiments, a bathroom and a sample collection room may be connected via a passageway configured for passing a sample from the bathroom to the sample collection room.

The methods, rooms, and systems disclosed herein are suited for providing subjects with pleasant surroundings, and convenient access to locations where a sample may be obtained for analysis. The methods, rooms, and systems disclosed herein a provide methods and means for obtaining samples from subjects in a pleasant and convenient manner. Thus, the methods, rooms, and systems disclosed herein provide advantages to subjects who wish to provide a sample (e.g., a clinical sample for medical analysis or diagnosis) and provide advantages over the art.

Accordingly, Applicants disclose embodiments of systems for obtaining samples, and systems for analyzing samples, including at least the following.

A room in a retail location configured for obtaining a blood sample including warming table, a calming feature, and a chair, the room being configured for obtaining a clinical sample such as a blood sample. In embodiments, the chair is a reclining chair.

A room in a retail location configured for obtaining a blood sample including a warming table, a calming feature, a pass-through to an adjacent bathroom, and a reclining chair.

A room in a retail location configured for obtaining a blood sample including a warming table, a calming feature, adjustable lighting, a pass-through to an adjacent bathroom, and a reclining chair.

A room in a retail location configured for obtaining a blood sample including a warming table, a calming feature, adjustable lighting, calming scents, a pass-through to an adjacent bathroom, and a reclining chair.

A room in a retail location configured for obtaining a blood sample including a warming table, a calming feature, a calming image, calming sounds, adjustable lighting, calming scents, a pass-through to an adjacent bathroom, and a reclining chair.

A room in a retail location configured for obtaining a blood sample including a warming table, a calming feature, a calming image, calming sounds, calming colors, adjustable lighting, calming scents, a pass-through to an adjacent bathroom, and a reclining chair.

Applicants disclose methods for obtaining samples, and for analyzing samples, including the following methods.

A method for obtaining a sample from a subject, the subject having a body part, comprising: providing a sample collection room in a retail store; and obtaining a sample from the body part of the subject, wherein the obtaining is performed in the sample collection room.

A method for analyzing a sample obtained from a subject, the subject having a body part, comprising: providing a sample collection room in a retail store; obtaining, in the sample collection room, a sample from the body part of the subject; and analyzing the sample at or adjacent to the retail store.

In at least one embodiment described herein, a method is provided for obtaining a sample from a subject, the method comprising: obtaining, in a sample collection room, a sample from said body part of said subject, wherein the sample obtained comprises capillary blood in a volume between about 10 to about 400 µL; and performing at least one HSV1 assay on said. sample.

For any of the embodiments herein, optionally, the volume of capillary blood collected is in the range of about 50 to about 400 µL. Optionally, the collected volume of capillary blood is in the range of about 100 to about 400 µL. Optionally, the collected volume of capillary blood is in the range of about 150 to about 400 µL. Optionally, the collected volume of capillary blood is in the range of about 200 to about 400 µL. Optionally, the collected volume of capillary blood is from one or more fingerstick puncture sites.

In at least one embodiment described herein, a method is provided of performing an assay on an instrument, the method comprising: storing assay cartridge in a pouch at a temperature above freezing, between 2 to 4° C.; scanning a sample container identifier on a sample container into SampleID field of the tracking file; opening cartridge pouch and discard pouch and desiccant in biohazard bin; scanning cartridge identifier on the cartridge into Barcode field of a tracking file and enter data into the PatientID field; orienting the cartridge such that an indicator on the cartridge confirms that cartridge is correctly aligned with the instrument; transferring 20-40 µL of plasma using a pipette into a vessel highlighted with a visual indicator on the cartridge; displaying instructions prompts on a display of instrument to insert the cartridge into the instrument and to start testing; inserting the cartridge into the instrument; once the cartridge is pulled into the instrument, the display will indicate that processing is initializing; once initialization is complete, the instrument automatically executes the protocol and the display will show a circular indicator displaying a percentage of the total time to execute the protocol, and an estimated countdown of the time remaining to complete the protocol; when the protocol is successfully completed, a "complete" message will appear briefly indicating that the process completed successfully, followed by a "Test complete" screen on the display; displaying an Eject Screen on the display to indicate that the test has been completed and the cartridge may be ejected by pressing the button; opening a cartridge door on the instrument and ejecting the cartridge, wherein the cartridge door will remain open for up to a threshold period of time after which the instrument retracts the cartridge and shuts the cartridge door to maintain the temperature within the instrument, in that case, the screen will go back to the Eject Screen; discarding the cartridge into a biohazard bin; and once the ejected cartridge is removed, the instrument detects such removal and the cartridge door will close and the display will navigate back to the Home Screen.

For any of the embodiments herein, the cartridge may kept right-side-up as indicated by a sticker on the top side of each pouch around each cartridge. Optionally, once the instrument has initialized, the Home Screen will appear; tapping the Home Screen to begin processing. Optionally, one embodiment of the method comprises tapping on the Home Screen to bring user to the Open Screen. Optionally, one embodiment of the method comprises touching the Open Button to open the cartridge door on the front of the instrument, starting a countdown timer. Optionally, if the cartridge is not inserted within the 90-second period, the door will close, and if this happens, the screen will go back to the Open Screen; pressing the Open Button to reopen the cartridge door.

In at least one embodiment described herein, a method is provided for processing a sample from a subject in an instrument, the method comprising: once a cartridge with the sample is loaded into the instrument, the following steps are automatically implemented in sequence over approximately a period of time less than a threshold time period; mixing diluent with sample plasma, negative control material and positive control material to yield sample diluent and diluted control samples in separate vessels; during a first incubation step, reacting HSV-1 IgG antibodies present in the controls and sample to bind an HSV-1 glycoprotein G (gG) recombinant antigen on a coated surface; following the first incubation step, removing unbound materials with a wash cycle; adding the detection reagent-AP conjugate and during a second incubation step, reacting a detection reagent-AP conjugate with HSV-1 IgG antibodies already bound to the capture surface; following the second incubation, removing unbound materials with a wash cycle; adding a chemiluminescent substrate to a capture-analyte-detection complex during a third incubation step to initiate the chemiluminescence reaction; and detecting light generated by the reaction and analyzed by the instrument using a calibration function to determine the cut-off index (COI) values for the sample.

For any of the embodiments herein, the coated surface comprises a coated surface of at least one bead. Optionally, the coated surface comprises a plurality of coated beads, each with a coated surface. Optionally, the coated surface comprises a coated surface of at least one pipette tip. Optionally, the threshold time period is between about 60 to about 80 minutes.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

DETAILED DESCRIPTION

Description and disclosure of examples of obtaining samples and of sample analysis methods, devices, and systems, including automated analysis devices, semi-automated analysis devices, and systems comprising such devices, which may be used with the methods and systems disclosed herein may be found, for example, in U.S. Pat. Nos. 8,088,593; 8,380,541; U.S. patent application Ser. No. 13/769,820, filed Feb. 18, 2013; PCT/US2012/57155, filed Sep. 25, 2012; U.S. Application Ser. No. 61/673,245, filed Sep. 26, 2011; U.S. Pat. No. 8,088,593; in U.S. Pat. No. 8,380,541; in International Patent Application PCT/US2013/052141, filed Jul. 25, 2013; U.S. patent application Ser. No. 13/244,947 filed Sep. 26, 2011; and in U.S. application Ser. No. 13/244,946, filed Sep. 26, 2011; the disclosures of all which patents and patent applications are hereby incorporated by reference in their entireties.

It is to be understood that both the foregoing general description and the following detailed description are exemplary and explanatory only and are not restrictive of the invention, as claimed. It may be noted that, as used in the specification and the appended claims, the singular forms "a", "an" and "the" include plural referents unless the context clearly dictates otherwise. Thus, for example, reference to "a material" may include mixtures of materials, reference to "a compound" may include multiple compounds, and the like. References cited herein are hereby incorporated by reference in their entirety, except to the extent that they conflict with teachings explicitly set forth in this specification.

In this specification and in the claims which follow, reference will be made to a number of terms which shall be defined to have the following meanings:

"Optional" or "optionally" means that the subsequently described circumstance may or may not occur, so that the description includes instances where the circumstance occurs and instances where it does not. For example, if a device optionally contains a feature for a sample collection unit, this means that the sample collection unit may or may not be present, and, thus, the description includes both structures wherein a device possesses the sample collection unit and structures wherein sample collection unit is not present.

As used herein, the terms "substantial" means more than a minimal or insignificant amount; and "substantially" means more than a minimally or insignificantly. Thus, for example, the phrase "substantially different", as used herein, denotes a sufficiently high degree of difference between two numeric values such that one of skill in the art would consider the difference between the two values to be of statistical significance within the context of the characteristic measured by the values. Thus, the difference between two values that are substantially different from each other is typically greater than about 10%, and may be greater than about 20%, preferably greater than about 30%, preferably greater than about 40%, preferably greater than about 50% as a function of the reference value or comparator value.

As used herein, the term "point of service location" (POS) may include locations where a subject may receive a service (e.g. testing, monitoring, treatment, diagnosis, guidance, sample collection, ID verification, medical services, non-medical services, etc.), and may include, without limitation, a subject's home, a subject's business, the location of a healthcare provider (e.g., doctor), hospitals, emergency rooms, operating rooms, clinics, health care professionals' offices, laboratories, retailers [e.g. pharmacies (e.g., retail pharmacy, clinical pharmacy, hospital pharmacy), drugstores, supermarkets, grocers, etc.], transportation vehicles (e.g. car, boat, truck, bus, airplane, motorcycle, ambulance, mobile unit, fire engine/truck, emergency vehicle, law enforcement vehicle, police car, or other vehicle configured to transport a subject from one point to another, etc.), traveling medical care units, mobile units, schools, day-care centers, security screening locations, combat locations, health assisted living residences, government offices, office buildings, tents, bodily fluid sample acquisition sites (e.g. blood collection centers), sites at or near an entrance to a location that a subject may wish to access, sites on or near a device that a subject may wish to access (e.g., the location of a computer if the subject wishes to access the computer), a location where a sample processing device receives a sample, or any other point of service location described elsewhere herein.

As used herein, a "sample", or "biological sample", or "clinical sample" refers to a sample of fluid, tissue, secretion, or excretion obtained from a subject. A clinical sample may be a sample of blood, serum, plasma, saliva, sputum, urine, gastric fluid, digestive fluid, tears, sweat, stool, semen, vaginal fluid, interstitial fluid, fluid derived from tumorous tissue, ocular fluids, mucus, earwax, oil, glandular secretions, spinal fluid, skin, cerebrospinal fluid from within the skull, tissue, fluid or material from a nasal swab, a throat swab, a cheek swab, or nasopharyngeal wash, biopsy fluid or material, placental fluid, amniotic fluid, cord blood, lymphatic fluids, cavity fluids, pus, microbiota obtained from a subject, meconium, breast milk, or other secretion or excretion. A sample may be a breath sample, a hair sample, a fingernail sample, or other sample.

Biological samples may include nasopharyngeal wash, or other fluid obtained by washing a body cavity or surface of a subject, or by washing a swab following application of the swab to a body cavity or surface of a subject. Nasal swabs, throat swabs, stool samples, hair, finger nail, ear wax, breath, and other solid, semi-solid, or gaseous samples may be processed in an extraction buffer, e.g., for a fixed or variable amount of time, prior to their analysis. The extraction buffer or an aliquot thereof may then be processed similarly to other fluid samples if desired. Examples of tissue samples of the subject may include but are not limited to, connective tissue, muscle tissue, nervous tissue, epithelial tissue, cartilage, cancerous sample, or bone. The sample may be obtained from a human or animal. The sample may be obtained from a vertebrate, e.g., a bird, fish, or mammal, such as a rat, a mouse, a pig, an ape, another primate (including humans), a farm animal, a sport animal, or a pet. The sample may be obtained from a living or dead subject. The sample may be obtained fresh from a subject or may have undergone some form of pre-processing, storage, or transport.

Thus, as used herein, a "sample" may be but is not limited to a blood sample, or a portion of a blood sample, may be of any suitable size or volume, and is preferably of small size or volume. In some embodiments of the assays and methods disclosed herein, measurements may be made using a small volume blood sample, or no more than a small volume portion of a blood sample, where a small volume comprises no more than about 5 mL; or comprises no more than about 3 mL; or comprises no more than about 2 mL; or comprises no more than about 1 mL; or comprises no more than about 500 µL; or comprises no more than about 250 µL; or comprises no more than about 100 µL; or comprises no more than about 75 µL; or comprises no more than about 50 µL; or comprises no more than about 35 µL; or comprises no more than about 25 µL; or comprises no more than about 20 µL; or comprises no more than about 15 µL; or comprises no more than about 10 µL; or comprises no more than about 8 µL; or comprises no more than about 6 µL; or comprises no more than about 5 µL; or comprises no more than about 4 µL; or comprises no more than about 3 µL; or comprises no more than about 2 µL; or comprises no more than about 1 µL; or comprises no more than about 0.8 µL; or comprises no more than about 0.5 µL; or comprises no more than about 0.3 µL; or comprises no more than about 0.2 µL; or comprises no more than about 0.1 µL; or comprises no more than about 0.05 µL; or comprises no more than about 0.01 µL.

As used herein, a "small volume" refers to a volume of less than about 1 mL, or less than about 500 µL, or less than about 250 µL, or less than 150 µL, or less than about 100 µL, or less than about 50 µL, or less than about 25 µL, or less. In particular embodiments, a small volume, such as a "finger-stick" volume, may comprise less than about 250 µL, and typically comprises less than 150 µL, or less than about 100 µL, or less than about 50 µL, or less than about 25 µL, or less.

As used herein, a "short period of time" refers to a period of time of about 5 hours or less, or about 4 hours or less, or about 3 hours or less, or about 2 hours or less, or about 1 hour or less, or about 50 minutes or less, or about 40 minutes or less, or about 30 minutes or less, or about 20 minutes or less, or about 10 minutes or less, or about 5 minutes or less. A short period of time may be determined with respect to an initial time; the initial time may be the time at which a sample analysis began; the initial time may be the time at which a sample is inserted into a device for the analysis of the sample; the initial time may be the time at which a sample was obtained from a subject.

It should be understood that embodiments in this disclosure may be adapted to have one or more of the features described below.

By way of non-limiting example, the Theranos™ HSV-1 IgG Assay is a chemiluminescent immunoassay intended for the qualitative detection of IgG antibodies to herpes simplex virus type 1 (HSV-1) in human serum, in K2-EDTA anticoagulated human plasma from venous blood, and in human fingerstick K2-EDTA anticoagulated whole blood obtained with the Theranos Capillary Tubes and Nanotainer Tubes at the Theranos Patient Service Centers and sent to a CLIA-certified laboratory for processing. By way of non-limiting example, some embodiments of such capillary Tubes and Nanotainer Tubes may be found in PCT Application Ser. Nos. PCT/US15/20307 and PCT/US13/000268, both fully incorporated herein by reference for all purposes. The test is indicated for sexually active individuals and expectant mothers as an aid in the presumptive diagnosis of HSV-1 infection. The predictive value of positive and negative results depends on the population's prevalence and the pretest likelihood of HSV-1. The Theranos HSV-1 IgG Assay is for use with the Theranos System which performs automated sample processing steps and result analysis. Although the Theranos System is described in the context of use with the HSV-1 assay, it should be understood that this merely exemplary and that the system and its principle(s) of operation are applicable to other assays alone or when processing multiple same or different assays in a multiplexed manner.

SUMMARY AND EXPLANATION OF THE TEST

HSV produces a wide variety of diseases. HSV transmission can result from direct contact with infected secretions from either a symptomatic or an asymptomatic host. HSV has been characterized into 2 distinct serotypes: HSV-1 and HSV-2. Many cases of genital herpes are transmitted by persons who are unaware that they are infected or do not recognize subtle or atypical symptoms.

One of the most serious consequences of genital herpes is neonatal herpes. Most mothers (70%) who transmit HSV to their children are asymptomatic at delivery. Transmission rates are much higher when the mother is experiencing a primary or initial genital infection (>50%) versus a recurrent infection (<5%), and where the mother is not yet producing IgG antibodies to HSV. Mothers are at greater risk for contracting a primary or initial genital HSV infection when they are seronegative to one or both HSV types, and their partner is seropositive.

Recently, HSV type-specific serological assays have been developed using the significant difference between the gG-1 protein of HSV-1 and the gG-2 of HSV-2.

By way of non-limiting example, the Theranos HSV-1 IgG Assay uses purified recombinant type-specific gG-1 antigen immobilized on polystyrene surface.

Note that as used in this Package Insert, the Theranos Patient Service Center is where fingerstick whole blood samples are collected and sent to a CLIA-certified laboratory for processing. Processing samples in the Theranos Patient Service Centers is limited to locations with a CLIA Certificate of Waiver. The CLIA Laboratory is where serum or EDTA-anticoagulated plasma samples are processed by the TSPU units in a CLIA-certified laboratory, after serum separation or plasma extraction steps, as applicable, have been performed off-board. A CLIA-certified laboratory is a clinical laboratory certified under the Clinical Laboratory Improvement Amendments of 1998 to perform non-waived testing.

Principle of the Procedure

The Theranos anti-HSV-1 IgG Assay is a three-step sandwich immunoassay with an HSV-1 glycoprotein G (gG) recombinant antigen coated surface, an anti-human IgG detection reagent conjugated to alkaline phosphatase (AP) and chemiluminescent substrate. During the first incubation step, the HSV-1 IgG antibodies present in the controls and sample bind to the gG recombinant antigen on the coated surface. Following the first incubation step, unbound materials are removed with a wash cycle. Then the detection reagent-AP conjugate is added and during the second incubation step, the detection reagent-AP conjugate reacts with the HSV-1 IgG antibodies already bound to the capture surface. Following the second incubation, unbound materials are removed with a wash cycle. The chemiluminescent substrate is added to the capture-analyte-detection complex during the third incubation step to initiate the chemiluminescence reaction. Light generated by this reaction is detected and analyzed by the Theranos System using a calibration function to determine the cut-off index (COI) values for the sample and controls. The results for the Positive and Negative controls may optionally be within specified limits for a run to be considered valid.

Materials Provided

Theranos Capillary Tubes and Nanotainer Tubes with K2-EDTA (Purple)

In one non-limiting example, the Theranos Capillary Tubes and Nanotainer Tubes are non-sterile, single use only collection devices consisting of two Capillary Tubes paired with two Nanotainer Tubes, that are capable of collecting, preserving, and transporting fingerstick whole blood samples for use with the Theranos HSV-1 IgG Assay. Each capillary is coated with di-potassium EDTA (K2-EDTA) anticoagulant which is intended to preserve the specimen during transport and/or storage (there are no anticoagulants in the Nanotainer Tubes). A needle interfaces with each capillary to transport blood from each capillary into a dedicated Nanotainer Tube.

Theranos Cartridge (HSV-1 IgG Assay)

In one non-limiting example, the Theranos HSV-1 IgG Assay reagents are assembled in a self-contained, ready-to-use pouched cartridge that is sufficient to run one test. The pouched cartridge should be removed from the refrigerator at least 10 minutes prior to use, but may optionally be used within 24 hours after removal from the refrigerator. Any cartridge that has exceeded the 24 hour time limit should be discarded. The cartridge pouch should be kept sealed until it is desired to run a sample. The components of the cartridge are described in Table 1 below:

TABLE 1

| Description of Materials Provided with the Theranos HSV-1 IgG Assay | |
|---|---|
| Capture surface | Coated with HSV-1 8G-1 recombinant antigen solution containing stabilizers and preservatives |
| Detection reagent (65 µL) | Mouse monoclonal antibody against human IgG, conjugated to alkaline phosphatase (AP) in a solution containing stabilizers and preservatives |
| Positive control (65 µL) | Liquid, human serum based, containing HSV-1 IgG. |
| Negative control (65 µL) | Liquid, human serum based, containing no HSV-1 IgG. |
| Assay Diluent (160 µL) | Phosphate buffered saline |
| Wash | Buffer (65 µL) TBS with detergent |
| Chemiluminescent AP substrate reagent (65 µL) | Proprietary fomulation |

Theranos TSPU Device

In one non-limiting example, the Theranos TSPU Device performs automated sample processing and signal detection. Raw data collected are analyzed by the Theranos System under the oversight of the Theranos CLIA-certified laboratory. The Theranos TSPU is intended to be used only with Theranos assay cartridges.

Other Optional Materials

- Disposable gloves—gloves may optionally be worn during the sample collection procedure. Gloves may optionally be worn during the sample processing procedure.
- Disposable absorbent workplace cover—for use in the sample collection procedure, to cover the workplace area used for sample collection. For use in the sample processing procedure, to cover the clean, flat workplace surface where the cartridge and sample are handled for sample processing on the TSPU device.
- Antiseptic wipes—for use in the sample collection procedure, to cleanse the patient's fingerstick sample collection site.
- Disinfectant wipes—if required during sample collection procedure, following sample transfer from Capillary Tubes to Nanotainer Tubes, to wipe any excess blood from the outside of the Nanotainer Tubes.
- Sterile safety lancet—single use, disposable, for use in the sample collection procedure to create the fingerstick puncture site.
- Warming device—commercially available, single use, disposable, for use in the sample collection procedure. It is recommended that the patient's finger is warmed for 45 seconds using the warming device prior to the skin puncture.
- Sterile gauze—for use in the sample collection procedure, to wipe any excess blood from the patient's fingertip following sample collection.
- Biohazard bin—For use in the sample processing procedure, to dispose of the used cartridge following sample processing, for use following the sample collection procedure to dispose of single use articles in contact with blood.
- Sharps container—for use in the sample collection procedure, to dispose of the used safety lancet.
- K2-EDTA Tube—a standard K2-EDTA collection tube for venipuncture (if required).

Warnings and Precautions

1. Performance characteristics of this assay have been determined with serum, venous K2-EDTA plasma, capillary K2-EDTA plasma and fingerstick whole blood K2-EDTA specimens collected in Theranos Capillary Tubes and Nanotainers.
2. All blood products should be treated as potentially infectious. Source materials from which this product (including controls) was derived have been screened for Hepatitis B surface antigen, Hepatitis C antibody and HIV-1/2 (AIDS) antibody by FDA-approved methods and found to be negative. However, as no known test methods can offer 100% assurance that products derived from human blood will not transmit these or other infectious agents, all controls, serum specimens and equipment coming into contact with these specimens should be considered potentially infectious and decontaminated or disposed of with proper biohazard precautions. CDC and the National Institutes of Health (NIH) recommend that potentially infectious agents be handled at the Biosafety Level 2.
3. Follow universal safety precautions. After adding patient or control specimens, the cartridges should be considered potentially infectious and handled accordingly.
4. Sodium azide at a concentration of 0.05% has been added to some reagents as an antibacterial agent. To prevent buildup of explosive metal azides in lead and copper plumbing, those reagents (see MATERIALS PROVIDED, above) should be discarded into sewerage only if diluted and flushed with large volumes of water. Use copper-free and lead-free drain systems where possible. Occasionally decontaminate the drains with 10% sodium hydroxide (CAUTION: caustic), allow to stand for 10 minutes, then flush with large volumes of water.
5. Do not substitute or mix reagents from or in, the cartridge. Only use the protocol described in this Package Insert.
6. Bacterial contamination of serum specimens or reagents can produce erroneous results. Use aseptic techniques to avoid microbial contamination.
7. Wear appropriate personal protective equipment (PPE) including suitable lab coat, disposable gloves and protective goggles when performing this procedure. Wash hands thoroughly after performing the test.

Preparation of the Reagents

In one non-limiting example, the Theranos HSV-1 IgG Assay reagents are packaged in a ready-to-use pouched cartridge as described above and are designed to be used directly. In this non-limiting example, no additional preparation of reagents is required. Pouched cartridges should be stored at 4° C. They should be kept right-side-up as indicated by a sticker on the top side of each pouch. When ready to use, the cartridge pouch should be opened and the wrapper and the desiccant should be discarded in a biohazard container.

Storage and Stability of the Reagents/Cartridge

When not in use, the Theranos HSV-1 IgG Assay cartridge should be stored upright at 2-8° C. When the cartridge is stored unopened, the reagents are stable at 2-8° C. up to 4 weeks. Do not freeze.

Always check the expiry date on the label. The cartridge should not be used past the expiry date indicated on the label. If an expired cartridge is inserted into the TSPU, it will be rejected.

The Theranos HSV-1 IgG Assay cartridge is designed for single use only. Unopened cartridges are stable until the expiry date as indicated on the label. Once opened, the Theranos HSV-1 IgG Assay cartridge should be used within 6 hours and should not be returned to storage. If not used immediately, the opened cartridge should be safely disposed of in a biohazard container in accordance with the guidelines or requirements of local, state and/or federal regulations or accreditation organizations. Do not recycle used cartridges.

Instruments: The TSPU Device

The Theranos HSV-1 IgG Assay is intended to be run on the Theranos™ TSPU Device only. Please refer to the Package Insert of the Theranos™ TSPU Device.

Theranos Patient Service Centers—Specimen Collection and Preparation

In one non-limiting example, the Theranos HSV-1 IgG Assay is intended for use with K2-EDTA anticoagulated human plasma from fingerstick whole blood. Fingerstick whole blood samples should be collected with the Theranos Capillary Tubes and Nanotainer Tubes in accordance with the instructions in the Reference Guide provided separately.

This device is designed to collect 80 µL of whole blood in each of a pair of Nanotainer Tubes (160 µL of whole blood in the paired Tubes).

CAUTION: All specimens may optionally be treated as potentially infectious material.

CLIA Laboratory—Specimen Collection and Preparation

In one non-limiting example, the Theranos HSV-1 IgG Assay is intended for use with human serum from venous blood and K2-EDTA anticoagulated human plasma from venous and fingerstick whole blood. Venous blood should be collected aseptically using approved venipuncture techniques by qualified personnel. For the collection of fingerstick specimens, fingerstick whole blood samples should be collected with the Theranos Capillary Tubes and Nanotainer Tubes in accordance with the instructions in the Quick Reference Guide provided separately. For the serum specimens collected by venipuncture, the blood should be allowed to clot, and the serum separated from the clot as soon as possible. Store and ship Nanotainer Tubes in controlled insulated and refrigerated containers specified by Theranos, following Nanotainer Tubes sample storage and shipment instructions as specified by Theranos. Store and ship venous samples in controlled insulated and refrigerated containers specified by Theranos, following venous sample storage and shipment instructions as specified by Theranos.

Upon receipt in the CLIA-certified laboratory; the fingerstick whole blood samples in the Nanotainer Tubes should be centrifuged at 1200 g for 5 minutes within 48 hours of sample collection. The venous K2-EDTA anticoagulated whole blood samples should be centrifuged at 1300 g for 10 minutes per standard vacutainer protocols.

The separated plasma from fingerstick specimens can remain at room temperature for no longer than 6 hours. If the assay will not be completed within 6 hours, refrigerate the sample at 2 to 8° C. If the assay will not be completed within 48 hours of storing at 2-8° C., the samples should be frozen at −20° C. Frozen specimens should be thawed and mixed well prior to use. A maximum of 3 freeze thaw cycles are allowed.

In this non-limiting example, the minimum volume used from the sample in the collection device is approximately 30 µL of specimen (plasma or serum) (10 µL of specimen is used for the assay and approximately 20 µL of dead volume).

CAUTION: All specimens may optionally be treated as potentially infectious material.

CLIA Laboratory—the HSV-1 Assay Procedure

To ensure proper test performance, in one non-limiting example, strictly adhere to the following operating instructions:

1. Pouched "HSV-1 IgG Assay, CLIA lab location" cartridges should be stored at 4° C. They should be kept right-side-up as indicated by a sticker on the top side of each pouch.
2. For fingerstick whole blood samples provided in the Capillary Tubes and Nanotainer Tubes:
   a. Scan QR code on bottom of Nanotainer Tube into SampleID field of the tracking file.
   b. Open cartridge pouch labelled "HSV-1 IgG Assay, CLIA lab location" and discard wrapper and desiccant in biohazard bin.
   c. Scan QR code on side of cartridge into Barcode field of tracking file and enter the patient number into the PatientID field.
   d. Orient the cartridge such that the barcode is on the right hand side and the Nanotainer Tube slot is on the upper right. The green arrow on the cartridge should point into the device.
   e. Transfer 30 µL of plasma using a manual pipette into the round vessel highlighted with a red ring near the center of the "Theranos HSV-1 IgG Assay, CLIA lab location" cartridge.
3. For venous blood collected with a commercially available venous blood EDTA-anti-coagulated collection device or commercially available serum collection device:
   a. Scan barcode on the sample container into SampleID field of the tracking file.
   b. Open cartridge pouch labelled "HSV-1 IgG Assay, CLIA lab location" and discard wrapper and desiccant in biohazard bin.
   c. Scan QR code on side of cartridge into Barcode field of tracking file and enter the patient number into the PatientID field.
   d. Orient the cartridge such that the barcode is on the right hand side and the Nanotainer Tube slot is on the upper right. The green arrow on the cartridge should point into the device.
   e. Transfer 30 µL of plasma or serum using a manual pipette into the round vessel highlighted with a red ring near the center of the "Theranos HSV-1 IgG Assay, CLIA lab location" cartridge.
4. Prompts on the TSPU touch screen should be followed to insert the cartridge into the TSPU and to start the test run.
5. Once the TSPU application has initialized, the Home Screen will appear. Tap the Home Screen to begin.
6. Tapping on the Home Screen brings you to the Open Screen.
7. Touch the Open Button to open the cartridge door on the front of the TSPU. This will start a 90-second countdown timer.
8. If the cartridge is not inserted within the 90-second period, the door will close. If this happens, the screen will go back to the Open Screen (Step 6). Press the Open Button to reopen the cartridge door (Step 7).
9. Insert the cartridge so its green arrow points into the TSPU. Upon detection, the TSPU will pull the cartridge into the TSPU.
10. Once the cartridge is pulled into the TSPU, the screen will indicate that the processing is initializing.
11. Once the initialization is complete, the TSPU will automatically execute the protocol and the screen will display a circular indicator displaying the percentage of the total time to execute the protocol in its center, and an estimated countdown of the time remaining to complete the protocol.
12. When the protocol is successfully completed, a "complete" message will appear briefly indicating that the process completed successfully, followed by a "Test complete" screen.
13. The final Eject Screen will indicate that the test has been completed and the cartridge may be ejected by pressing the button.
14. The door will open and the cartridge will be ejected. The door will remain open for up to 120 seconds at which time the TSPU retracts the cartridge and shuts the door to maintain the temperature within the TSPU. In that case, the screen will go back to the Eject Screen (Step 13).
15. The cartridge should then be discarded into a biohazard bin.
16. The TSPU detects once the ejected cartridge is removed, and the cartridge door will close and navigate back to the Home Screen.

Once the cartridge is loaded into the TSPU the following steps are automatically implemented in sequence over approximately 78 minutes.
1. Sample plasma, negative control material and positive control material are mixed with sample diluent to yield sample diluent and diluted control samples in separate vessels.
2. During the first incubation step, the HSV-1 IgG antibodies present in the controls and sample bind an HSV-1 glycoprotein G (gG) recombinant antigen on a coated surface.
3. Following the first incubation step, unbound materials are removed with a wash cycle.
4. Then the detection reagent-AP conjugate is added and during the second incubation step, the detection reagent-AP conjugate reacts with the HSV-1 IgG antibodies already bound to the capture surface.
5. Following the second incubation, unbound materials are removed with a wash cycle.
6. The chemiluminescent substrate is added to the capture-analyte-detection complex during the third incubation step to initiate the chemiluminescence reaction.
7. Light generated by this reaction is detected and analyzed by the Theranos System using a calibration function to determine the cut-off index (COI) values for the sample.

Quality Control (Qc)

The Theranos HSV-1 IgG Assay cartridges are completely self-contained and ready-to-use, and include the use of on-board positive and negative controls. Each laboratory should establish its own QC ranges and frequency of QC testing based on applicable local laws, regulations and standard good laboratory practice. The on-board positive and negative controls are purchased from commercial sources. These on-board control samples are run simultaneously with the assay each time a patient sample is run, processed in parallel with the patient samples, in exactly the same way as the patient sample is processed.

| Expected Control Results | |
|---|---|
| Control Type | Expected Result |
| Positive Control: Liquid (65 µL), human serum based, containing HSV-1 IgG | Positive |
| Negative Control: Liquid (65 µL), human serum based, containing no HSV-1 IgG. | Negative |

The output from these control runs are analyzed by the Theranos System for any performance deficiencies in the system in real time, thereby helping to ensure that the sample output is accurate. Calibration functions consists of pass/fail limits, for both the positive control and the negative control. If the control value lies outside the pass limit, the run is considered to be invalid. If either control fails or if it is out of range, the test result will be INVALID as described in Table 2 below.

Interpretation of Results

The result returned by the Theranos HSV-1 IgG test automatically factors in the validity of on-board controls. The user obtains a result with one of the following possibilities:

TABLE 2

| Interpretation of Results | | |
|---|---|---|
| Result | Interpretation. | Follow up Testing Recommendation |
| POSITIVE | HSV-1 specific IgG antibodies detected | None |
| NEGATIVE | HSV-1 specific IgG antibodies not detected | None |
| EQUIVOCAL | HSV-1 specific IgG antibody status equivocal | CLIA Laboratory: Samples should be re-tested. If on re-test, the sample is still equivocal, then a second sample should be drawn within 4-6 weeks and tested. |
| INVALID | Invalid result | The test result should be discarded and the test should be re-run. |

Clinical Studies
1. Expected Values:
The Theranos HSV-1 IgG Assay was used to evaluate the prevalence of HSV-1 IgG antibodies in individuals for whom an HSV-1 IgG test was ordered by a physician including pregnant women. The study populations for the Theranos HSV-1 IgG Assay consisted of a total of 558 subjects, with 260 sexually active adults and 298 individuals identified as pregnant women. The result for 1 out of the 558 subjects is not reported, as indicated in Table 3 (1 subject), giving a total of 557 subjects. The data for the intended use population (557 specimens) have been summarized according to age group in decades, gender, number of reactive results, and number of non-reactive results. The data for the intended use population have been summarized in Table 3 (259 specimens from sexually active adult subjects) and Table 4 (298 specimens from pregnant subjects).

TABLE 3

| Expected Results for Theranos HSV-1 IgG Assay in Adult Subjects | | | | |
|---|---|---|---|---|
| Age Range | Gender | Reactive N/Total (%) | Equivocal N/Total (%) | Non-Reactive N/Total (%) |
| 16 to 19 | Male | 0/0 (0) | 0/0 (0) | 0/0 (0) |
| 16 to 19 | Female | 1/4 (25) | 0/4 (0) | 3/4 (75) |
| 20 to 29 | Male | 8/18 (44.4) | 1/18 (5.6) | 9/18 (50) |
| 20 to 29 | Female | 29/73 (39.7) | 0/73 (0) | 44/73 (60.3) |
| 30 to 39 | Male | 5/10 (50) | 0/10 (0) | 5/10 (50) |
| 30 to 39 | Female | 33/62 (53.2) | 0/62 (0) | 29/62 (46.8) |
| 40 to 49 | Male | 5/10 (50) | 0/10 (0) | 5/10 (50) |
| 40 to 49 | Female | 16/27 (59.3) | 0/27 (0) | 11/27 (40.7) |
| 50 to 59 | Male | 17/20 (85) | 0/20 (0) | 3/20 (15) |
| 50 to 59 | Female | 9/11 (81.8) | 0/11 (0) | 2/11 (18.2) |
| 60 to 69 | Male | 5/6 (83.3) | 0/6 (0) | 1/6 (16.7) |

TABLE 3-continued

Expected Results for Theranos HSV-1 IgG Assay in Adult Subjects

| Age Range | Gender | Reactive N/Total (%) | Equivocal N/Total (%) | Non-Reactive N/Total (%) |
|---|---|---|---|---|
| 60 to 69 | Female | 5/10 (50) | 1/10 (10) | 4/10 (40) |
| 70 to 79 | Male | 3/4 (75) | 0/4 (0) | 1/4 (25) |
| 70 to 79 | Female | 1/3 (33.3) | 0/3 (0) | 2/3 (66.7) |
| 80 to 89 | Male | 0/0 (0) | 0/0 (0) | 0/0 (0) |
| 80 to 89 | Female | 1/1 (100) | 0/1 (0) | 0/1 (0) |
| Total* | | 138/259 (53.3) | 2/259 (0.8) | 119/259 (45.9) |

*1 sample not reported since age information was not available

TABLE 4

Expected Results for Theranos HSV-1 IgG Assay in Pregnant Subjects

| Age Range | Gender | Reactive N/Total (%) | Equivocal N/Total (%) | Non-Reactive N/Total (%) |
|---|---|---|---|---|
| 18 to 19 | Female | 13/13 (100) | 0/13 (0) | 0/13 (0) |
| 20 to 29 | Female | 114/175 (65.1) | 1/175 (0.6) | 60/175 (34.3) |
| 30 to 39 | Female | 61/104 (58.7) | 0/104 (0) | 43/104 (41.3) |
| 40 to 49 | Female | 5/6 (83.3) | 0/6 (0) | 1/6 (16.7) |
| Total | | 193/298 (65) | 1/298 (0.3) | 104/298 (35) |

The hypothetical positive and negative predictive values (PPV, NPV) for the two intended use populations are shown in Table 5. The calculations are based on the specificity and sensitivity values for the Theranos HSV-1 IgG Assay determined in the clinical study;
1. Specificity of 97.4% and Sensitivity of 95.1% in adults
2. Specificity of 95.2% and Sensitivity of 97.4% in pregnant women

TABLE 5

Hypothetical Predictive Values

| | High Risk Adults | | Pregnant Women | |
|---|---|---|---|---|
| Prevalence (%) | PPW (%) | NPV (%) | PPV (%) | NPV (%) |
| 50 | 93.8 | 92.6 | 92.1 | 91.7 |
| 45 | 93.2 | 93.2 | 91.3 | 92.4 |
| 40 | 92.4 | 93.8 | 90.3 | 93.0 |
| 35 | 91.4 | 94.2 | 89.1 | 93.5 |
| 30 | 90.1 | 94.6 | 87.5 | 94.0 |
| 25 | 88.3 | 94.9 | 85.3 | 94.3 |
| 20 | 85.8 | 95.2 | 82.3 | 94.7 |
| 15 | 82.0 | 95.5 | 77.7 | 95.0 |
| 10 | 75.2 | 95.7 | 69.9 | 95.2 |
| 5 | 60.2 | 96.0 | 53.8 | 95.5 |

2. Clinical Performance in the Intended Use Populations (CLIA Laboratory Model):

A clinical study was conducted to characterize the performance of the Theranos HSV-1 IgG Assay in the Theranos CLIA-certified Laboratory in comparison to the FOCUS HerpeSelect Immunoblot (as the reference method for performance analysis).

Prospectively collected, archived venous serum samples collected from pregnant women and sexually active adults (18 years and older) who had a prescription for a HSV-1 IgG test. Samples were obtained from multiple specimen sources covering 10 US states and Mexico.

The equivocal results on the Focus HerpeSelect Immunoblot (that repeatedly tested equivocal) were resolved using a validated western blot reference test (University of Washington, Seattle) as per the instructions of the package insert for the reference method. Ten samples from the sexually active adult sub-population tested initially equivocal on the Focus HerpeSelect Immunoblot and were resolved by the University of Washington western blot as 2 negatives and 7 positives. One sample was not resolved. There were no samples in the sexually active adult sub-population that returned an invalid result.

In the pregnant women sub-population, 8 samples tested initially equivocal on the Focus HerpeSelect immunoblot. Of these, 4 samples could not be resolved by University of Washington western blot due to insufficient volume availability. Of the remaining 4, 1 (one) were resolved as negative and 3 as positive. There were 3 samples that returned an invalid result on the Theranos HSV-1 IgG test. These samples were rerun and resulted in valid results included in the analysis.

TABLE 6

Summary of Theranos HSV-1 IgG Test Performance with Sexually Active Adult Population

| | | Reference method | | | |
|---|---|---|---|---|---|
| | | Positive | Equivocal | Negative | Total |
| Equivocal | Positive | 137 | 0 | 2 | 139 |
| HSV-1 | Theranos | 1 | 0 | 1 | 2 |
| IgG | Negative | 5 | 1 | 113 | 119 |
| Assay | Total | 143 | 1 | 116 | 260 |

| | Point Estimate | 95% Confidence Interval |
|---|---|---|
| Sensitivity | 95.1% (137/144) | 90.3-97.6 |
| Specificity | 97.4% (113/116) | 92.7-99.1 |

TABLE 7

Summary of Theranos HSV-1 IgG Test Performance with Pregnant Women Population

| | | Reference method | | | |
|---|---|---|---|---|---|
| | | Positive | Equivocal | Negative | Total |
| Theranos | Positive | 188 | 1 | 4 | 193 |
| HSV-1 | Equivocal | 0 | 1 | 0 | 1 |
| IgG | Negative | 2 | 2 | 100 | 104 |
| Assay | Total | 190 | 4 | 104 | 298 |

| | Point Estimate | 95% Confidence Interval |
|---|---|---|
| Sensitivity | 97.9% (188/192) | 94.8-99.2 |
| Specificity | 95.2% (100/105) | 89.3-98.0 |

3. CDC Panel Testing:

The objective of this study was to demonstrate agreement of the Theranos HSV-1 IgG Assay with the CDC panel.

A panel of well characterized serum samples (n=100) was obtained from the US Centers for Disease Control and Prevention (CDC). The CDC sample panel was tested with the HSV-1 IgG Assay and the results obtained by Theranos were sent to the CDC for confirmation. The panel consisted of 54 positives and 46 negatives. The Theranos HSV-1 IgG Assay demonstrated 100% agreement with the results provided by the CDC.

4. Low Prevalence Population:

Serum samples were collected from a low prevalence population: individuals who are not sexually active, and without a recent or current sexually transmitted disease (Hepatitis, Syphilis, HIV, HPV, *Trichomonas, Chlamydia, Gonorrhoeae*) as determined in an interview. Performance of the assay on this population is summarized in Table 8. The Samples were obtained from multiple specimen sources covering 10 US states and Mexico.

TSPU devices, three (3) lots of cartridges and sixteen (16) operators in total. The study duration was 13 days in total. Details of the study design for different samples are presented in Table 9 below.

TABLE 9

Design of Precision Study: Numbers of Replicates, Devices, Days and Operators

| Panel Member | Valid Replicates | | | | No. of Devices | No. of Days | No. of Operators | No. of Invalid Replicates |
|---|---|---|---|---|---|---|---|---|
| | Total | Lot 1 | Lot 2 | Lot 3 | | | | |
| A | 91 | 26 | 38 | 27 | 35 | 7 | 14 | 3 |
| B | 88 | 24 | 37 | 27 | 28 | 7 | 14 | 2 |
| C | 78 | 27 | 44 | 8 | 35 | 8 | 16 | 3 |
| D | 80 | 25 | 27 | 28 | 11 | 2 | 4 | 4 |
| E | 64 | 25 | 13 | 26 | 13 | 2 | 6 | 1 |
| F | 69 | 25 | 19 | 25 | 15 | 2 | 4 | 3 |

Results of the precision study are presented in Table 10.

TABLE 10

Summary of Precision Study Results

| Panel Member | Mean (COI) | | Repeatability (same device, same lot) | Between-device | Between-lot | Precision (same device, different lot) | Precision (different device, same lot) | Precision (different device, different lot) |
|---|---|---|---|---|---|---|---|---|
| A | 0.425 | SD | 0.049 | 0.007 | 0.000 | 0.049 | 0.049 | 0.049 |
| | | % CV | 11.5% | 1.6% | 0% | 11.5% | 11.6% | 11.6% |
| B | 0.648 | SD | 0.086 | 0.011 | 0.029 | 0.091 | 0.087 | 0.092 |
| | | % CV | 13.3% | 1.7% | 4.5% | 14.1% | 13.4% | 14.2% |
| C | 1.016 | SD | 0.093 | 0.062 | 0.065 | 0.113 | 0.112 | 0.129 |
| | | % CV | 9.1% | 6.1% | 6.4% | 11.1% | 11.0% | 12.7% |
| D | 1.727 | SD | 0.208 | 0.098 | 0.013 | 0.208 | 0.230 | 0.230 |
| | | % CV | 12.0% | 5.7% | 0.8% | 12.0% | 13.3% | 13.3% |
| E | 3.809 | SD | 0.305 | 0.276 | 0.108 | 0.324 | 0.411 | 0.425 |
| | | % CV | 8.0% | 7.3% | 2.8% | 8.5% | 10.8% | 11.2% |
| F | 8.996 | SD | 0.807 | 0.437 | 0.000 | 0.807 | 0.918 | 0.918 |
| | | % CV | 9.0% | 4.9% | 0.0% | 9.0% | 10.2% | 10.2% |

TABLE 8

Summary of Theranos HSV-1 IgG Assay Performance with Low Prevalence Population

| | | Reference method | | | |
|---|---|---|---|---|---|
| | | Positive | Equivocal | Negative | Total |
| Theranos HSV-1 IgG Assay | Positive | 32 | 0 | 0 | 32 |
| | Equivocal | 0 | 0 | 0 | 0 |
| | Negative | 0 | 1 | 49 | 50 |
| | Total | 32 | 1 | 49 | 82 |

| | Point Estimate | 95% Confidence Interval |
|---|---|---|
| Sensitivity | 97.0% (32/33) | 84.7-99.5 |
| Specificity | 100% (49/49) | 92.7-100 |

P Analytical Performance Studies

5. Precision—CLIA Laboratory Model, Venous Serum

A study for estimating precision of Theranos HSV-1 IgG Assay for venous serum samples in a CLIA Laboratory model was performed by testing a panel of 6 serum samples spanning the analytical range [negative (A), high negative (B), equivocal (C), low positive (D), moderate positive (E), and positive (F)]. The precision study was conducted at one site with thirty five (35)

Table 11 presents percent of invalid results and percents of negative, equivocal and positive among valid results for each sample.

TABLE 11

Percent of Invalid Results and Percents of Negative, Equivocal and Positive among Valid Results

| Panel Member | Mean (COI) | Number of Replicates | Percent of Invalid | Percent of Negative among Valid | Percent of Equivocal among Valid | Percent of Positive among Valid |
|---|---|---|---|---|---|---|
| A | 0.425 | 94 | 3.2% (3/94) | 100% (91/91) | | |
| B | 0.648 | 90 | 2.2% (2/90) | 100% (88/88) | | |
| C | 1.016 | 81 | 3.7% (3/81) | 17.9% (14/78) | 60.3% (47/78) | 21.8% (17/78) |
| D | 1.727 | 84 | 4.8% (4/84) | | | 100% (80/80) |
| E | 3.809 | 65 | 1.5% (1/65) | | | 100% (64/64) |
| F | 8.996 | 72 | 4.2% (3/72) | | | 100% (69/69) |

The results of the study demonstrate that the precision of the Theranos HSV-1 IgG Assay (including different TSPU devices, different lots of cartridges, and different operators) when performed in a CLIA Laboratory was in the range 10.2% to 14.2%.

6. Precision—CLIA Laboratory Model, Fingerstick Whole Blood

A study for estimating the precision of the Theranos HSV-1 IgG Assay for fingerstick whole blood samples in a CLIA Laboratory model was performed by testing a panel of 3 fingerstick plasma samples spanning the analytical range [high negative (P), equivocal (Q), moderate positive (R)]. The precision study was conducted at one site with thirty-six (36) TSPU devices, three (3) lots of cartridges and nine (9) operators in total. The study duration was 4 days in total. Details of the study design for different samples are presented in Table 12 below.

TABLE 12

Design of Precision Study Numbers of Replicates, Devices, Days and Operators

| Panel Member | Valid Replicates | | | | No. of Devices | No. of Days | No. of Operators | No. of Invalid Replicates |
|---|---|---|---|---|---|---|---|---|
| | Total | Lot 1 | Lot 2 | Lot 3 | | | | |
| P | 168 | 56 | 56 | 56 | 36 | 4 | 9 | 3* |
| Q | 168 | 56 | 56 | 56 | 29 | 4 | 9 | 2* |
| R | 168 | 56 | 56 | 56 | 27 | 4 | 9 | 2* |

*All invalid replicates were repeated

Results of the precision study are presented in Table 13.

TABLE 13

Summary of Precision Study Results

| Panel Member | Mean (COI) | | Repeatability (same device, same lot) | Between-device | Between-lot | Precision (same device, different lot) | Precision (different device, same lot) | Precision (different device, different lot) |
|---|---|---|---|---|---|---|---|---|
| P | 0.888 | SD | 0.083 | 0.006 | 0.050 | 0.096 | 0.083 | 0.097 |
| | | % CV | 9.3% | 0.7% | 5.6% | 10.9% | 9.3% | 10.9% |
| Q | 1.047 | SD | 0.094 | 0.025 | 0.069 | 0.117 | 0.098 | 0.119 |
| | | % CV | 9.0% | 2.4% | 6.6% | 11.1% | 9.3% | 11.4% |
| R | 3.241 | SD | 0.342 | 0.122 | 0.157 | 0.377 | 0.363 | 0.396 |
| | | % CV | 10.6% | 3.8% | 4.9% | 11.6% | 11.2% | 12.2% |

Table 14 presents percent of invalid results and percents of negative, equivocal and positive among valid results for each sample.

TABLE 14

Percents of Positive, Equivocal, Negative and Invalid Results

| Panel Member | Mean (COI) | Number of replicates | Percent of Invalid | Percent of negative among valid | Percent of equivocal among valid | Percent of positive among valid |
|---|---|---|---|---|---|---|
| P | 0.888 | 171 | 1.8% (3/171) | 58.3% (98/168) | 40.5% (68/168) | 1.2% (2/168) |
| Q | 1.047 | 170 | 1.2% (2/170) | 6.5% (11/168) | 63.1% (106/168) | 30.4% (51/168) |
| R | 1.016 | 170 | 1.2% (2/170) | | | 100% (168/168) |

The results of the study demonstrate that the precision of the Theranos HSV-1 IgG Assay (including different TSPU devices, different lots of cartridges, and different operators) when performed in a CLIA Laboratory was in the range from 10.9% to 12.2%.

7. Reproducibility:

In one non-limiting example, a study designed to process multiple fingerstick whole blood samples from individual subjects was performed to evaluate the reproducibility of the Theranos HSV-1 IgG Assay when used with Theranos Capillary Tubes and Nanotainer Tubes. The study was conducted at 3 collection sites with 10 subjects at each site. From each of 30 subjects, 9 Capillary Tubes and Nanotainer Tubes from 3 manufacturing lots (i.e. 3 Capillary Tubes and Nanotainer Tubes per lot) and 2 serum separator tubes (SSTs) were collected. Each subject had following measurements:

Each of the 9 Capillary Tubes and Nanotainer Tubes was tested. These data were used for evaluation of between-Capillary Tubes and Nanotainer Tubes imprecision, between-lot imprecision and total imprecision that includes between-Capillary Tubes and Nanotainer Tubes and between-lot imprecisions.

One Nanotainer Tube (from one of the 3' lot of Capillary Tubes and Nanotainer Tubes for each subject) was tested in duplicate via recovering a sample from one Capillary Tubes and Nanotainer Tubes and transferring a sample to another Capillary Tubes and Nanotainer Tubes. These data were used for evaluation of within-Capillary Tubes and Nanotainer Tubes imprecision.

Each of the 2 SSTs was tested. These data were used for evaluation of between-SST imprecision.

For samples with mean COI value at the baseline ≥0.5, percent differences were calculated and for samples with mean COI value at the baseline <0.5, differences were calculated. Table 15 summarizes the results of the precision study broken down by collection site and by high or low COI subjects; the variability metrics are averaged across all subjects within the site.

TABLE 15

Summary of Results of the Precision Study

Capillary Tubes and Nanotainer Tubes

| Collection Site | Subjects | Within-Capillary Tubes and Nanotainer Tubes (% CV or SD) | Between-Capillary Tubes and Nanotainer Tubes (% CV or SD) | Between-Lot (% CV or SD) | Total (% CV or SD) | SST Between-SST (% CV or SD) |
|---|---|---|---|---|---|---|
| 1 | 6 subjects with COI values 1.4-13.5 | % CV = 6.0% | % CV = 9.0% | % CV = 6.8% | % CV = 12.6% | % CV = 9.6% |
|   | 4 subjects with COI values 0.03-0.28 | SD = 0.008 | SD = 0.015 | SD = 0.016 | SD = 0.024 | SD = 0.11 |
| 2 | 7 subjects with COI values 1.6-16.8 | % CV = 8.2% | % CV = 9.2% | % CV = 3.2% | % CV = 10.8% | % CV = 12.5% |
|   | 3 subjects with COI values 0.07-0.19 | SD = 0.009 | SD = 0.011 | SD = 0.008 | SD = 0.015 | SD = 0.019 |
| 3 | 5 subjects with COI values 4.5-14.3 | % CV = 8.2% | % CV = 8.1% | % CV = 6.0% | % CV = 11% | % CV = 12.4% |
|   | 5 subjects with COI values 0.02-0.32 | SD = 0.08 | SD = 0.019 | SD = 0.013 | SD = 0.025 | SD = 0.021 |
| Combined | 18 subjects with COI values 1.4-16.8 | % CV = 7.5% | % CV = 8.8% | % CV = 5.2% | % CV = 11.4% | % CV = 11.5% |
|   | 12 subjects with COI values 0.02-0.32 | SD = 0.008 | SD = 0.015 | SD = 0.013 | SD = 0.022 | SD = 0.017 |

Within-Capillary Tubes and Nanotainer Tubes imprecision was % CV=7.5% for aggregated subjects with mean COI ≥0.5 and SD=0.008 for aggregated subjects with mean COI <0.5.

Total imprecision including between-Capillary Tubes and Nanotainer Tubes and between-lot imprecisions was % CV=11.4% for aggregated subjects with mean COI ≥0.5 and SD=0.022 for aggregated subjects with mean COI <0.5.

Between—serum separator tubes imprecision was % CV=11.5% for aggregated subjects with mean COI ≥0.5 and SD=0.017 for aggregated subjects with mean COI <0.5.

8. Analyte Stability

An analyte stability study was performed to characterize the stability of HSV-1 IgG in clinical matrices as measured by the Theranos HSV-1 IgG Assay under different sample storage conditions and time periods. A summary of analyte storage conditions and durations for different sample types and matrices claimed for the Theranos HSV-1 IgG Assay is presented in Table 16.

TABLE 16

Summary of Analyte Storage Conditions and Durations

| Condition | Venous Serum | Venous K2-EDTA Plasma | Fingerstick K2-EDTA Plasma | Fingerstick K2-EDTA Whole Blood |
|---|---|---|---|---|
| Stored at 2-8° C. | 48 hr | 48 hr | 48 hr | 48 hr |
| Stored at room temperature (20-25° C) | 6 hr | 6 hr | 6 hr | 6 hr |
| Stored at −20° C | 1 week | 1 week | 1 week | N/A |
| Freeze/thaw cycles | 3 | 3 | 3 | N/A |

Within 2 hours after collection, one aliquot of each sample type or matrix was tested with the Theranos HSV-1 IgG Assay in duplicate, to establish the value at baseline. The samples were stored in Nanotainer Tubes under the appropriate conditions. Comparison of an average of two replicates at the predetermined time points with the average of two replicates at baseline was performed: for samples with mean COI value at the baseline ≥0.5, percent differences were calculated and for samples with mean COI value at the baseline <0.5, differences were calculated.

Acceptance criteria were as follows: i) a difference averaged over all samples with baseline mean COI value ≥0.5 may optionally be less than ±10% and a difference averaged over all samples with baseline COI mean <0.5 may optionally be less than 0.02 and ii) for each sample, an observed difference may optionally be less than 15% for the samples with baseline mean COI value ≥0.5 and may optionally be less than 0.08 for the samples with baseline mean COI value <0.5 (the range of differences expected if there is no effect of storage on the HSV-1 IgG analyte).

TABLE 17

Summary of Mean Absolute Difference Measures for all Storage Conditions and Sample Types or Matrices

| Sample Type and Matrix | | Samples with Baseline COI < 0.5 | | Samples with Baseline COI > 0.5 | |
| --- | --- | --- | --- | --- | --- |
| | | Difference averaged over all samples | The largest observed difference among samples | Percent difference averaged over all samples | The largest observed percent difference among samples |
| Stored at 2–8° C., 48 hrs | Venous serum | 0.006 | 0.006 | 1.0% | 13.6% |
| | Venous K2 EDTA plasma | −0.007 | −0.007 | 2.3% | 13.3% |
| | Fingerstick K2-EDTA plasma from whole blood | 0.003 | 0.003 | −0.4% | 13.9% |
| Stored at −20, 1 week | Venous serum | 0.008 | 0.015 | 0.8% | 13.3% |
| | Venous K2-EDTA plasma | 0.003 | 0.005 | −1.0% | 12.7% |
| | Fingerstick K2-EDTA plasma from whole blood | 0.001 | 0.008 | 1.8% | −13.9% |
| Freeze Thaw Cycles, n = 3 | Venous serum | 0.007 | 0.021 | −0.1% | 13.6% |
| | Venous K2-EDTA plasma | 0.021 | 0.037 | −1.7% | −13.4% |
| | Fingerstick K2-EDTA plasma from whole blood | 0.006 | 0.022 | −1.0%7 | 13.6% |
| Stored at room temp, 6 hrs | Venous serum | −0.001 | −0.011 | −3.2% | −11.9% |
| | Venous K2-EDTA plasma | 0.002 | 0.022 | 0.1% | 13.7% |
| | Fingerstick K2-EDTA plasma from whole blood | −0.004 | −0.026 | 1.1% | 13.9% |

9. Interfering Substances:

A study was designed and performed (in accordance with CLSI EP07-A2) to evaluate the performance of the Theranos HSV-1 IgG Assay in the presence of potentially interfering substances to assess the impact of these endogenous substances and commonly used drugs on the performance of the Theranos HSV-1 IgG Assay. Interferents were tested with three serum samples (negative (mean COI 0.024), high negative (mean COI 0.77) and low positive (mean COI 1.52)) that were contrived by using a high positive sample and diluting it with pooled negative serum. Samples were spiked with the interferent at levels shown in Table 18. Each serum pool was tested in duplicate.

For the low positive and the high negative pools, the acceptance criteria were a mean recovery within +/−20% of the value of the unspiked sample (i.e., in the absence of the potential interferent or drug). All low positive and high negative samples showed a signal change of less than 15% for all interfering substances. All positive samples remained positive and all negative samples remained negative upon spiking of drug or other interferents. For the negative pool, the acceptance criterion was a deviation of less than 0.02 COI. All negative samples showed a mean deviation of ≤0.02 COI, except Intralipid. Intralipid spikes did not show any effect on recovery for near cut-off samples, high negative and low positive samples.

TABLE 18

Summary of Interfering Substances Studies: Endogenous Interferents and Drug Interferents

| Iterferent | Level | | Negative Pool | | High Negative Pool | | Low Positive Pool | |
| --- | --- | --- | --- | --- | --- | --- | --- | --- |
| | | | Mean COI | ΔCOI | Mean COI | % Recovery | Mean COI | % Recovery |
| Hemoglobin | 1000 | mg/dL | 0.025 | 0.00 | 0.69 | 90 | 1.71 | 113 |
| Bilirubin | 20 | mg/dL | 0.024 | 0.00 | 0.68 | 88 | 1.61 | 106 |
| Intralipid | 2000 | mg/dL | 0.053 | 0.03 | 0.81 | 105 | 1.60 | 105 |
| Acetylcysteine | 150 | mg/dL | 0.019 | −0.004 | 0.68 | 88 | 1.40 | 92 |
| Ampicillin-Na | 1000 | mg/dL | 0.025 | 0.001 | 0.76 | 99 | 1.44 | 95 |

TABLE 18-continued

Summary of Interfering Substances Studies: Endogenous Interferents and Drug Interferents

| Iterferent | Level | Negative Pool Mean COI | ΔCOI | High Negative Pool Mean COI | % Recovery | Low Positive Pool Mean COI | % Recovery |
|---|---|---|---|---|---|---|---|
| Ascorbic acid | 300 mg/dL | 0.027 | 0.003 | 0.75 | 97 | 1.67 | 110 |
| Ca-Dobesilate | 200 mg/dL | 0.027 | 0.004 | 0.70 | 91 | 1.51 | 99 |
| Cyclosporine | 5 mg/dL | 0.031 | 0.008 | 0.74 | 97 | 1.53 | 101 |
| Cefoxitin | 2500 mg/dL | 0.027 | 0.003 | 0.74 | 97 | 1.52 | 100 |
| Heparin | 5000U | 0.020 | −0.003 | 0.80 | 103 | 1.52 | 100 |
| Levodopa | 20 mg/dL | 0.030 | 0.006 | 0.68 | 88 | 1.42 | 94 |
| Methyldopa+1.5h20 | 20 mg/dL | 0.024 | 0.000 | 0.74 | 97 | 1.37 | 90 |
| Metronidazole | 200 mg/dL | 0.039 | 0.016 | 0.74 | 96 | 1.38 | 91 |
| Phenylbutazone | 400 mg/dL | 0.021 | −0.002 | 0.74 | 96 | 1.42 | 94 |
| Doxycycline | 50 mg/dL | 0.024 | 0.000 | 0.71 | 92 | 1.35 | 89 |
| Acetylsalicylic acid | 1000 mg/dL | 0.026 | 0.002 | 0.75 | 97 | 1.37 | 90 |
| Rifampicin | 60 mg/dL | 0.014 | −0.009 | 0.69 | 90 | 1.35 | 89 |
| Acetaminophen | 200 mg/dL | 0.034 | 0.010 | 0.64 | 83 | 1.68 | 111 |
| Control | | 0.024 | 0.000 | 0.77 | 100 | 1.52 | 100 |

10. Cross-Reactivity:

A study was performed to evaluate the performance of the Theranos HSV-1 IgG Assay in the presence of IgG antibodies against twenty-one (21) infectious agents defined as potential cross-reactants in the FDA guidance on HSV serological assays. Banked serum samples confirmed positive for IgG against the infectious agents of interest were acquired from commercial vendors. At least three (3) samples, independently confirmed as positive for that agent and negative for HSV-1 IgG on the reference method, were tested on the Theranos HSV-1 IgG Assay in order to rule out cross-reactivity of the Theranos HSV-1 IgG Assay with IgG against a potential cross reactant. The results of this study are displayed in Table 19 below.

TABLE 19

Summary of Cross-reactivity Study Results

| Organism/ Condition | No. | Reference HSV-1 Assay | Theranos HSV-1 Positive | Theranos HSV-1 Negative | Theranos HSV-1 Equivocal |
|---|---|---|---|---|---|
| Epstein Barr Virus (IgG) | 6 | Negative | 0 | 6 | 0 |
| Epstein Barr Virus (IgM) | 1 | Negative | 0 | 1 | 0 |
| HPV | 4 | Negative | 0 | 4 | 0 |
| Rubella (IgG) | 13 | Negative | 0 | 13 | 0 |
| HSV-2 (IgG) | 40 | Negative | 0 | 40 | 0 |
| HAMA samples | 4 | Negative | 0 | 4 | 0 |
| Treponona pallidum | 8 | Negative | 0 | 7 | 1* |
| Rheumatoid Factor (RF) | 8 | Negative | 1** | 7 | 0 |
| Anti-nuclear antibody (ANA) | 8 | Negative | 0 | 8 | 0 |
| Sjogren's Syndrome | 3 | Negative | 0 | 3 | 0 |
| CMV (IgG) | 5 | Negative | 0 | 5 | 0 |
| CMV (IgM) | 2 | Negative | 0 | 2 | 0 |
| Chlamydia trachomatis (IgG) | 10 | Negative | 0 | 10 | 0 |
| HCV (IgG) | 3 | Negative | 0 | 3 | 0 |
| HBsAg | 3 | Negative | 0 | 3 | 0 |
| VZV IgG | 5 | Negative | 0 | 5 | 0 |
| Measles IgG | 5 | Negative | 0 | 5 | 0 |
| HIV-1 (IgG) | 4 | Negative | 0 | 4 | 0 |
| Toxoplasma IgG | 4 | Negative | 0 | 4 | 0 |

TABLE 19-continued

Summary of Cross-reactivity Study Results

| Organism/ Condition | No. | Reference HSV-1 Assay | Theranos HSV-1 Positive | Theranos HSV-1 Negative | Theranos HSV-1 Equivocal |
|---|---|---|---|---|---|
| Candida albicans Ag | 3 | Negative | 0 | 3 | 0 |
| Systemic Lupus | 3 | Negative | 0 | 3 | 0 |

*Systematic cross-reactivity ruled out (7/8 samples in same categoty tested negative)
**Confirmed as positive upon retest; systematic cross-reactivity ruled out (7/8 samples in same categmy tested negative)

11. Assay Cut-Off:

A study was performed to establish the cut-off and the limits of the equivocal zone for the Theranos HSV-1 IgG Assay using 192 serum samples. Then 120 independent serum samples were analyzed to validate the established cut-off. The calibrators were assigned COI values based on the established assay cut-off, the cut-off for positive results a COI of 1.1 and cut-off for negative results a COI of 0.9. The results of the cut-off validation study are displayed in Table 20 below.

TABLE 20

Performance of Selected Cut-off on Independent Sample Set

| Agreement Classification | Percent Agreement | 95% Confidence Interval |
|---|---|---|
| NPA | 96.0% (47/49) | 86.3-98.9 |
| PPA | 97.1% (69/71) | 90.3-99.2 |

Method Comparison Studies

12. Fingerstick Plasma—CLIA Laboratory Model:

To demonstrate the performance of the Theranos HSV-1 IgG Assay for fingerstick whole blood, samples were collected at 3 Theranos Patient Service Centers (TPSCs) and processed at the CLIA-certified laboratory. At each site, fingerstick whole blood samples were collected into a pair of Theranos Capillary Tubes and Nanotainer Tubes, and venous samples were collected into serum tubes from 20, 16 and 25 adult subjects at three collection sites.

Samples were shipped refrigerated to the Theranos CLIA-certified laboratory in Palo Alto, Calif. Upon receipt, fingerstick whole blood samples in the Nanotainer Tubes were centrifuged at 1200 g for 5 minutes. Plasma was extracted and processed and analyzed on the Theranos System. All samples were processed or frozen as plasma within 48 hours of draw. The venous samples were processed into serum for testing with the reference method (FOCUS HerpeSelect Immunoblot).

A summary of the performance information is shown in the following Table 21:

TABLE 21

Summary of Method Comparison for Samples Collected at 3 Theranos Patient Service Centers

|  |  | Reference Result | |
| --- | --- | --- | --- |
|  |  | POS | NEG |
| Theranos Result | POS | 38 | 0 |
|  | NEG | 1 | 22 |

|  | Point Estimate | 95% Confidence Interval |
| --- | --- | --- |
| Sensitivity | 97.4% (38/39) | 86.8-99.6 |
| Specificity | 100% (22/22) | 85.1-100 |

Figure 1:
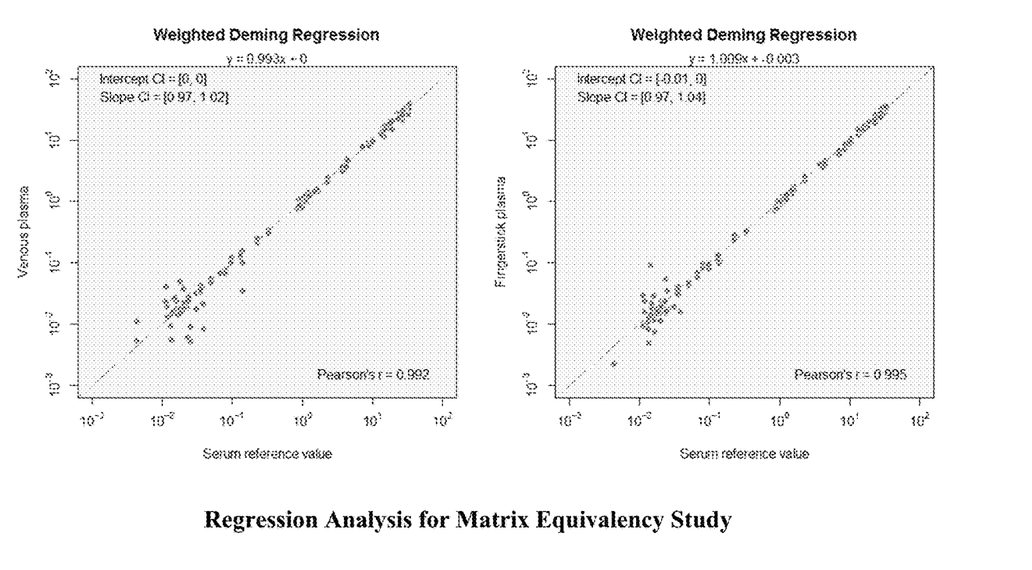
FIG. 1 shows data for at least one embodiment as described herein.

13. Matrix Comparison:

The effect of anticoagulants and different sample types (fingerstick and venous) on the performance of the Theranos HSV-1 IgG Assay was determined by comparing matched venous serum, venous K2-EDTA plasma, and fingerstick K2-EDTA plasma samples from 70 donors. Forty-three matched sample sets were contrived to have analyte values close to the cut-off. The acceptance criterion was a recovery of positive plasma samples within ±20% of the corresponding serum reference value (serum drawn into primary tubes without gel). For negative samples, the acceptance criteria was a difference of <=0.02 COI from the corresponding serum value. All anticoagulant-treated plasma samples met this criterion. Weighted Deming regression was performed. The slope and intercept of the regression line and their 95% confidence intervals along with correlation coefficients are shown in Table 22 and a graphical depiction is shown in FIG. 1.

TABLE 22

Summary of Weighted Deming Regression Analysis Performed on Matrix Equivalency Data for Venous Plasma and Fingerstick Plasma Samples.

| Sample type/Matrix | Correlation coefficient | Slope | 95% confidence interval on slope | Intercept | 95% confidence interval on intercept |
| --- | --- | --- | --- | --- | --- |
| Venous a plasm | 0.992 | 0.993 | [0.967, 1.019] | 0.000 | [−0.003, 0.003] |
| Fingerstick plasma | 0.995 | 1.009 | [0.973, 1.044] | −0.003 | [−0.006, −0.001] |

Disposal

Theranos Patient Service Centers—All used safety lancets may optionally be disposed of in the sharps container. All used cartridges may optionally be disposed of in the biohazard bin. Any single use articles in contact with blood, such as gloves, gauze or wipes, may optionally be disposed of in the biohazard bin. Hazardous or biologically contaminated materials may optionally be disposed of in accordance with county, federal, state and local regulations.

CLIA Laboratory Model—All used cartridges are to be disposed of in the biohazard bin. Any single use articles in contact with blood may optionally be disposed of in the biohazard bin. Hazardous or biologically contaminated materials may optionally be disposed of in accordance with county, federal, state and local regulations.

In one non-limiting example, the Theranos™ HSV-1 IgG External Controls are for use with Theranos™ Herpes Simplex Virus-1 (HSV-1) IgG Assay. These quality control reagents are to be used according to the instructions in the HSV-1 IgG Assay Package Insert to provide additional confirmation of the cut-off calibration for each new lot of cartridges. Although described in the context of HSV-1, it should be understood that embodiments of the calibrator process, all calibrators on the cartridge that also has all assay reagents/disposables, and procedure herein is applicable to other assays run on the Theranos system. Optionally, all calibrators are on the cartridge that also has at least some of the assay reagents/disposables. Optionally, at least some assay calibrators are on the cartridge that also has at least some of the assay reagents/disposables. Optionally, at least some assay calibrators are on the cartridge that also has all of the assay reagents/disposables.

Optionally, a CLIA Waiver or other regulatory body waiver may be in place for processing at the Theranos Patient Service Centers.

REAGENTS

| Component (as labeled) | Qty. | Description | Mean value (COI) | Expected Range (COI) | Expected result |
| --- | --- | --- | --- | --- | --- |
| External Controls for HSV-1 IgG assay, Positive | 160 μL | Single-use, pre-dispensed (barcoded) pouched Nanotainer Tubes with pre-loaded external controls | 1.45 | 0.60-1.00 | POSITIVE |
| External Controls for HSV-1 IgG assay, Negative | 160 μL | Single-use, pre-dispensed (barcoded) pouched Nanotainer Tubes with pre-loaded external controls | 0.80 | 1.10-1.69 | NEGATIVE |

The values returned for positive and negative controls are auto-verified by the Theranos System by comparing to a predefined range of COI values for the particular lot of these controls.

Warnings and Precautions

1. For use with Theranos HSV-1 IgG Assay.
2. External controls are intended to be used once per new cartridge lot at each Theranos Patient Service Center. Failure to use these controls as intended will not allow for additional confirmation of the cut-off calibration for a new lot of cartridges.
3. External control materials should be handled, processed, and disposed of in a manner identical to patient samples.
4. Always check the expiry date. External control materials should not be used past the expiry date indicated on the pouch label.

Storage and Handling Requirements

In one non-limiting example, external control materials are shipped frozen to the Theranos Patient Service Centers. External control materials are to be stored frozen at −20° C.

Unopened external control materials are stable until the expiry date as indicated on the pouch label.

Assay Procedure

When ready to use, remove from the pouch and thaw at room temperature. Two separate cartridges should be used for processing the positive and the negative external controls. The Theranos HSV-1 IgG External Controls should be processed in a manner identical to processing of patient samples on the Theranos System. Please reference the test procedure section of the Theranos HSV-1 IgG Assay Package Insert for procedural instructions.

Additional details regarding the device and sample collection process can be found in PCT application WO2014088606 filed Sep. 5, 2013 and PCT application PCT/US14/30792 filed Mar. 17, 2014, each application fully incorporated herein by reference for all purposes.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

Additionally, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a size range of about 1 nm to about 200 nm should be interpreted to include not only the explicitly recited limits of about 1 nm and about 200 nm, but also to include individual sizes such as 2 nm, 3 nm, 4 nm, and sub-ranges such as 10 nm to 50 nm, 20 nm to 100 nm, etc.

The publications discussed or cited herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All publications mentioned herein are incorporated herein by reference to disclose and describe the structures and/or methods in connection with which the publications are cited.

U.S. Application Ser. No. 61/874,983, filed Sep. 6, 2013, U.S. application Ser. No. 14/020,785, filed Sep. 6, 2013, U.S. Application Ser. No. 62/010,421, filed Jun. 10, 2014, U.S. Patent Publication 2005/0100937, U.S. Pat. No. 8,380,541; U.S. Pat. App. Ser. No. 61/676,178, filed Jul. 26, 2012; U.S. Pat. App. Ser. No. 61/766,116, filed Feb. 18, 2013; U.S. Pat. App. Ser. No. 61/802,194, filed Mar. 15, 2013; U.S. patent application Ser. No. 13/769,798, filed Feb. 18, 2013; U.S. patent application Ser. No. 13/769,779, filed Feb. 18, 2013; U.S. patent application Ser. No. 13/244,947 filed Sep. 26, 2011; PCT/US2012/57155, filed Sep. 25, 2012; U.S. application Ser. No. 13/244,946, filed Sep. 26, 2011; U.S. patent application Ser. No. 13/244,949, filed Sep. 26, 2011; and U.S. Application Ser. No. 61/673,245, filed Sep. 26, 2011, the disclosures of which patents and patent applications are all hereby incorporated by reference in their entireties.

The following applications or documents are fully incorporated herein by reference for all purposes:

Centers for Disease Control and Prevention. Sexually transmitted diseases treatment guidelines 2002. MMWR 2002:5 1 (No. RR-6).

Arvin, A, C Prober. Herpes Simplex Viruses. 876-883. In Murray, P, E Baron, M Pfaller, F Tenover, and R Yolkenet (eds.). Manual of Clinical Microbiology. 6th Ed. ASM, Washington, D.C. (1995).

Whitley, R. Herpes Simplex Viruses. 2297-2231. In Fields, B, D Knipe, P Howley, et al. (eds.). Fields Virology 3rd Ed. Lippincott-Raven, Philadelphia. (1996).

Whitley, R, A Nahmias, A Visintine, C Fleming, C Alford. Natural history of herpes simplex virus infection of mother and newborn. Pediatrics 66:489-494 (1980).

Whitley, R. Herpes simplex, in J Klein & J Remington (ed.), Infectious diseases of the fetus and newborn infants, 3rd ed., p. 282-305.

Prober, C, W Sullender, L Yasukawa, D Au, A Yaeger, A Arvin. Low risk of herpes simplex virus infections in neonates exposed to the virus at the time of vaginal delivery to mothers with recurrent herpes simplex virus infections. N Engl J Med 316:240-244 (1987).

Brown, Z, S Sleke, J Zeh, J Kopelman, A Maslow, R Ashley, D Watts, S Berry, M Herd, L Correy. The acquisition of herpes simplex virus during pregnancy. N Engl J Med 337:509-515 (1997).

Prober C G, Corey L, Brown Z A et al. 1992. The management of pregnancies complicated by genital infections with herpes simplex virus. Clin Infect Dis. 15:1031-1038.

Brown Z A, Benedetti J, Ashley R et. al. 1991. Neonatal herpes simplex virus infection in relation to asymptomatic maternal infection at the time of labor. N Engl J Med. 324:1247-1252.

CDC-NIH Manual. (2009) Biosafety in Microbiological and Biomedical Laboratories. 5th ed.

Clinical and Laboratory Standards Institute (CLSI). Procedures for the Handling and Processing of Blood Specimens for Common Laboratory Tests; Approved Guideline-Fourth Edition. CLSI document GP44-A4.

Ashley-Morrow R, Krantz E, Wald A. Time Course of Seroconversion by HerpeSelect ELISA After Acquisition of Genital Herpes Simplex Virus Type 1 (HSV-1) or HSV-2. Sex Transm Dis. 2003 April; 30(4):3 10-314.

Ashley R L. Performance and use of HSV type-specific serology test kits. Herpes 2002 July; 9(2):38-45.

Liljeqvist et al. Typing of Clinical Herpes Simplex Virus Type 1 and Type 2 Isolates with Monoclonal Antibodies. J Clin Micro 37:2727-2718 (1999).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Any feature, whether preferred or not, may be combined with any other feature, whether preferred or not. The appended claims are not to be interpreted as including means-plus-function limitations, unless such a limitation is explicitly recited in a given claim using the phrase "means for." It should be understood that as used in the description herein and throughout the claims that follow, the meaning of "a," "an," and "the" includes plural reference unless the context clearly dictates otherwise. For example, a reference to "an assay" may refer to a single assay or multiple assays. Also, as used in the description herein and throughout the claims that follow, the meaning of "in" includes "in" and "on" unless the context clearly dictates otherwise. Finally, as used in the description herein and throughout the claims that follow, the meaning of "or" includes both the conjunctive and disjunctive unless the context expressly dictates otherwise. Thus, the term "or" includes "and/or" unless the context expressly dictates otherwise.

This document contains material subject to copyright protection. The copyright owner (Applicant herein) has no objection to facsimile reproduction of the patent documents and disclosures, as they appear in the US Patent and Trademark Office patent file or records, but otherwise reserves all copyright rights whatsoever. The following notice shall apply: Copyright 2015 Theranos, Inc.

What is claimed is:

1. A method for processing a sample from a subject in an instrument using a chemiluminescent immunoassay, the method comprising: after a cartridge with the sample, a first vessel, second vessel, and third vessel is loaded into the instrument, the following steps are automatically implemented in sequence by the instrument following a protocol over a period of time less than a threshold time period;
   processing the sample to extract sample plasma containing HSV-1 IgG antibodies;
   mixing diluent with sample plasma containing HSV-1 IgG antibodies, negative control material and positive control material containing HSV-1 IgG antibodies to yield sample plasma containing HSV-1 IgG antibodies diluent in the first vessel, diluted positive control sample in the second vessel, and diluted negative control sample in the third vessel;
   during a first incubation step, reacting HSV-1 IgG antibodies present in the diluted positive control sample and sample to bind an HSV-1 glycoprotein G (gG) recombinant antigen on a coated surface;
   following the first incubation step, removing unbound materials with a wash cycle;
   during a second incubation step, reacting a detection reagent-AP conjugate with the HSV-1 IgG antibodies already bound to the coated surface to form a capture-analyte-detection complex;
   following the second incubation, removing unbound materials with a wash cycle;
   adding a chemiluminescent substrate to the washed capture-analyte-detection complex during a third incubation step to initiate a chemiluminescence reaction; and
   detecting light generated by the chemiluminescence reaction and analyzed by the instrument using a calibration function.

2. The method of claim 1 wherein the coated surface comprises a coated surface of at least one bead.

3. The method of claim 1 wherein the threshold time period is between about 60 to about 80 minutes.

4. A method for processing a sample from a subject in an instrument using a chemiluminescent immunoassay, the method comprising:
   after a cartridge with the sample, a first vessel, second vessel, and third vessel is loaded into the instrument, the following steps are automatically implemented in sequence by the instrument following a protocol over a period of time less than a threshold time period;
   processing the sample to extract sample plasma containing HSV-1 IgG antibodies;
   mixing diluent with sample plasma containing HSV-1 IgG antibodies, negative control material and positive control material containing HSV-1 IgG antibodies to yield sample plasma containing HSV-1 IgG antibodies diluent in the first vessel, diluted positive control sample in the second vessel, and diluted negative control sample in the third vessel;
   during a first incubation step, reacting HSV-1 IgG antibodies present in the diluted positive control sample and sample to bind an HSV-1 glycoprotein G (gG) recombinant antigen on a coated surface;
   following the first incubation step, removing unbound materials with a wash cycle;
   during a second incubation step, reacting a detection reagent-AP conjugate with the HSV-1 IgG antibodies already bound to the coated surface to form a capture-analyte-detection complex;
   following the second incubation, removing unbound materials with a wash cycle;
   adding a chemiluminescent substrate to the washed capture-analyte-detection complex during a third incubation step to initiate a chemiluminescence reaction; and
   detecting light generated by the chemiluminescence reaction and analyzed by the instrument using a calibration function,
   wherein the coated surface comprises a plurality of coated beads, each with a coated surface.

5. A method for processing a sample from a subject in an instrument using a chemiluminescent immunoassay, the method comprising:
   after a cartridge with the sample, a first vessel, second vessel, and third vessel is loaded into the instrument, the following steps are automatically implemented in sequence by the instrument following a protocol over a period of time less than a threshold time period;
   processing the sample to extract sample plasma containing HSV-1 IgG antibodies;
   mixing diluent with sample plasma containing HSV-1 IgG antibodies, negative control material and positive control material containing HSV-1 IgG antibodies to yield sample plasma containing HSV-1 IgG antibodies diluent in the first vessel, diluted positive control sample in the second vessel, and diluted negative control sample in the third vessel;
   during a first incubation step, reacting HSV-1 IgG antibodies present in the diluted positive control sample and sample to bind an HSV-1 glycoprotein G (gG) recombinant antigen on a coated surface;
   following the first incubation step, removing unbound materials with a wash cycle;

during a second incubation step, reacting a detection reagent-AP conjugate with the HSV-1 IgG antibodies already bound to the coated surface to form a capture-analyte-detection complex;

following the second incubation, removing unbound materials with a wash cycle;

adding a chemiluminescent substrate to the washed capture-analyte-detection complex during a third incubation step to initiate a chemiluminescence reaction; and detecting light generated by the chemiluminescence reaction and analyzed by the instrument using a calibration function, wherein the coated surface comprises a coated surface of at least one pipette tip.

* * * * *